(12) United States Patent
Ludwin et al.

(10) Patent No.: US 11,006,853 B2
(45) Date of Patent: *May 18, 2021

(54) FIELD-BASED LOCATION COORDINATE CORRECTION

(71) Applicant: BIOSENSE WEBSTER (ISRAEL) LTD., Yokneam (IL)

(72) Inventors: Doron Moshe Ludwin, Haifa (IL); Eitan Peri, Givat Ada (IL); Eliahu Zino, Atlit (IL); Meir Bar-Tal, Haifa (IL); Shaul Haim Raz, Shimshit (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 363 days.

This patent is subject to a terminal disclaimer.

(21) Appl. No.: 15/228,555

(22) Filed: Aug. 4, 2016

(65) Prior Publication Data

US 2017/0065204 A1   Mar. 9, 2017

Related U.S. Application Data

(60) Provisional application No. 62/214,257, filed on Sep. 4, 2015.

(51) Int. Cl.
*A61B 5/06*     (2006.01)
*A61B 9/00*     (2006.01)
(Continued)

(52) U.S. Cl.
CPC ............. *A61B 5/063* (2013.01); *A61B 5/05* (2013.01); *A61B 5/053* (2013.01); *A61B 5/062* (2013.01);
(Continued)

(58) Field of Classification Search
None
See application file for complete search history.

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| CN | 102389334 A | * | 3/2012 | ............. A61B 34/20 |
| CN | 104812299 B | * | 10/2017 | ............. A61B 5/063 |

(Continued)

OTHER PUBLICATIONS

European Search Report, Application No. 16187037.3-1657, dated Feb. 6, 2017.

*Primary Examiner* — Matthew Kremer
(74) *Attorney, Agent, or Firm* — Notaro, Michalos & Zaccaria P.C.

(57) ABSTRACT

A method uses patches fixed to a surface of a body, the patches including respective electrodes in contact with the surface, and at least one of the patches configured to output a signal in response to a magnetic field applied to the body. Initially, the signal is processed to compute first magnetic locations and first electrical locations of the at least one of the patches. Subsequently, the signal is processed to compute second magnetic locations and second electrical locations of the at least one of the patches. A first relation is computed between the first magnetic and the first electrical locations, a second relation is computed between the second magnetic and the second electrical locations, and upon detecting a difference between the second and the first relations, a magnetic location correction is computed and then applied to track a position of a magnetic sensor inside the body.

16 Claims, 5 Drawing Sheets

(51) Int. Cl.
  *G16H 20/30* (2018.01)
  *G16H 40/60* (2018.01)
  *A61B 5/287* (2021.01)
  *A61B 5/361* (2021.01)
  *A61B 5/363* (2021.01)
  *A61B 5/05* (2021.01)
  *A61B 5/053* (2021.01)
  *A61B 5/00* (2006.01)
  *A61B 18/14* (2006.01)
  *A61B 90/00* (2016.01)
  *A61B 34/20* (2016.01)

(52) U.S. Cl.
  CPC .............. *A61B 5/287* (2021.01); *A61B 5/361* (2021.01); *A61B 5/363* (2021.01); *A61B 5/6833* (2013.01); *A61B 18/1492* (2013.01); *A61B 90/39* (2016.02); *G16H 20/30* (2018.01); *G16H 40/60* (2018.01); *A61B 5/6852* (2013.01); *A61B 2034/2051* (2016.02); *A61B 2090/3975* (2016.02); *A61B 2505/05* (2013.01)

(56) References Cited

U.S. PATENT DOCUMENTS

| | | |
|---|---|---|
| 5,558,091 A | 9/1996 | Acker et al. |
| 5,899,860 A | 5/1999 | Pfeiffer et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,574,498 B1 | 6/2003 | Gilboa |
| 6,690,963 B2 | 2/2004 | Ben-Haim et al. |
| 6,788,967 B2 | 9/2004 | Ben-Haim et al. |
| 7,751,868 B2 | 7/2010 | Glossop |
| 7,941,213 B2 | 5/2011 | Markowitz et al. |
| 8,060,185 B2 | 11/2011 | Hunter et al. |
| 8,456,182 B2 | 6/2013 | Bar-Tal et al. |
| 2005/0143648 A1* | 6/2005 | Minai .................... A61B 1/041 600/410 |
| 2007/0016007 A1 | 1/2007 | Govari et al. |
| 2008/0154285 A1 | 6/2008 | von Jako |
| 2009/0137883 A1* | 5/2009 | Chiba .................... A61B 1/041 600/302 |
| 2010/0079158 A1 | 4/2010 | Bar-Tal |
| 2012/0172702 A1 | 7/2012 | Koyrakh |
| 2012/0265054 A1 | 10/2012 | Olson |
| 2012/0302869 A1 | 11/2012 | Koyrakh |
| 2013/0066193 A1 | 3/2013 | Olson |

FOREIGN PATENT DOCUMENTS

| | | |
|---|---|---|
| EP | 2886054 A1 | 6/2015 |
| WO | 20140028114 A1 | 2/2014 |
| WO | 2014182822 A1 | 11/2014 |

* cited by examiner

FIELD-BASED LOCATION COORDINATE CORRECTION

CROSS-REFERENCE TO RELATED APPLICATION

This application claims the benefit of U.S. Provisional Patent Application 62/214,257, filed Sep. 4, 2015, which is incorporated herein by reference.

FIELD OF THE INVENTION

The present invention relates generally to medical imaging, and specifically to a method for correcting inconsistent field-based location coordinates of a skin patch affixed to a patient.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid field-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention for sensing, using an array of patches fixed to a surface of a body of a subject, the patches including respective electrodes in contact with the surface, and at least one of the patches including a patch sensor configured to output a signal in response to a magnetic field applied to the body, the method including at a first time, processing the signal so as to compute first field-based location coordinates of the at least one of the patches, and computing first impedance-based location coordinates of the at least one of the patches by measuring an impedance between the at least one of the patches and an electrode inside the body, at a second time, subsequent to the first time, processing the signal so as to compute second field-based location coordinates of the at least one of the patches, and computing second impedance-based location coordinates of the at least one of the patches by measuring the impedance between the at least one of the patches and the electrode inside the body, computing a first relation between the first field-based location coordinates and the first impedance-based location coordinates, and a second relation between the second field-based location coordinates and the second impedance-based location coordinates, when there is a difference between the second relation and the first relation, computing a field-based location coordinate correction responsively to the difference, and applying the field-based location coordinate correction in tracking a position of a magnetic tracking sensor inside the body, based on signals received from the magnetic tracking sensor in response to the applied magnetic field.

In embodiments of the present invention, the first relation for a given patch may include a first distance and a first orientation between the first impedance-based location coordinates of the given patch to the first field-based location coordinates of the given patch, and the second relation for the given patch may include a second distance and a second orientation between the second impedance-based location coordinates of the given patch to the second field-based location coordinates of the given patch. In some embodiments, the field-based location coordinate correction for the second field-based location coordinates of the given patch includes the first distance and the first orientation, and applying the field-based location coordinate correction includes computing corrected second field-based location coordinates based on the second impedance-based location coordinates and the first distance and the first orientation.

In additional embodiments, the method may include processing, at a third time subsequent to the second time, the signal so as to compute third field-based location coordinates of the at least one of the patches, computing third impedance-based location coordinates of the at least one of the patches by measuring the impedance to the electrical current, and applying the field-based location coordinate correction to the third field-based location coordinates. In further embodiments, the magnetic field is applied to the body by positioning the body over multiple coils configured to generate the magnetic field.

In supplemental embodiments, the sensor is included in a medical probe, and the electrode inside the body includes a probe electrode located at a distal end of the medical probe. In additional embodiments, the signal includes a first signal, and measuring the impedance includes receiving, from the at least one patches, a second signal in response to the impedance to the electrical current delivered by the probe electrode to the body.

There is also provided, in accordance with an embodiment of the present invention an apparatus for sensing, including an array of patches fixed to a surface of a body of a subject, the patches including respective electrodes in contact with the surface, and at least one of the patches including a patch sensor configured to output a signal in response to a magnetic field applied to the body, and a control console configured to process, at a first time, the signal so as to compute first field-based location coordinates of the at least one of the patches, and to compute first impedance-based location coordinates of the at least one of the patches by measuring an impedance between the at least one of the patches and an electrode inside the body, to process, at a second time subsequent to the first time, the signal so as to compute second field-based location coordinates of the at least one of the patches, and to compute second impedance-based location coordinates of the at least one of the patches by measuring the impedance between the at least one of the patches and the electrode inside the body, to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction responsively to the difference, and to apply the field-based location coordinate correction in tracking a position of a magnetic tracking sensor inside the body, based on signals received from the magnetic tracking sensor in response to the applied magnetic field.

There is further provided, in accordance with an embodiment of the present invention a computer software product, for sensing, using an array of patches fixed to a surface of a body of a subject, the patches including respective electrodes in contact with the surface, and at least one of the patches including a patch sensor configured to output a signal in response to a magnetic field applied to the body, the product including a non-transitory computer-readable medium, in which program instructions are stored, which instructions, when read by a computer, cause the computer to process, at a first time, the signal so as to compute first field-based location coordinates of the at least one of the patches, and to compute first impedance-based location coordinates of the at least one of the patches by measuring an impedance between the at least one of the patches and an electrode inside the body, to process at a second time, subsequent to the first time, the signal so as to compute second field-based location coordinates of the at least one of the patches, and to compute second impedance-based location coordinates of the at least one of the patches by measuring the impedance between the at least one of the patches and the electrode inside the body, to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction responsively to the difference, and to apply the field-based location coordinate correction in tracking a position of a magnetic tracking sensor inside the body, based on signals received from the magnetic tracking sensor in response to the applied magnetic field.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various diagnostic and therapeutic procedures involve mapping of the electrical potential on the inner surface of a cardiac chamber. Electrical mapping can be performed, for example, by inserting a medical probe (e.g., a catheter), whose distal end is fitted with a position sensor and a mapping electrode (also referred to herein as a probe electrode), into the cardiac chamber. The cardiac chamber is mapped by positioning the probe at multiple points on the inner chamber surface. At each point, the electrical potential is measured using the mapping electrode, and the distal end position is measured using the position sensor. The measurements are typically presented as a map of the electrical potential distribution over the cardiac chamber surface.

While positioning the medical probe within the cardiac chamber, impedance-based and/or magnetic field-based (also referred to herein as field-based) position sensing systems can be used to determine a location of the probe within the cardiac chamber. In impedance-based position sensing systems, such as those described in U.S. Pat. No. 8,456,182, whose disclosure is incorporated herein by reference, a set of adhesive skin patches is affixed to a subject's body, and a distal end of a medical probe (e.g., a catheter) is inserted into a body cavity of the subject.

The patches include respective electrodes in contact with a surface of the subject. Typically the set of patches comprises three or more patches. A control console delivers a current to an electrode (also referred to herein as an impedance-based location sensor) positioned at the distal end of the probe. Each of the patches receives a portion of the current, and conveys its respective received current back to the control console. From the received currents the control console can determine an impedance between each patch and the mapping electrode, and compute, based on the impedances, impedance-based location coordinates for the distal end. The impedance-based location coordinates are three-dimensional coordinates measured with respect to a frame of reference defined by the patches herein assumed to have impedance-based coordinates, and enable the distal end to be tracked in this frame of reference in the body cavity.

In field-based position sensing systems, multiple magnetic field generators may be positioned under the subject. A field-based position sensor, also herein termed a magnetic tracking sensor, is positioned at the distal end of the probe, and the sensor conveys a probe signal to the control console in response to the magnetic fields received from the field generators. Upon receiving the probe signal from the tracking sensor, the control console can compute, based on the probe signal, field-based probe location coordinates for the distal end. The field-based probe location coordinates are three-dimensional coordinates with respect to a frame of reference defined by field-based location coordinates of the magnetic field generators, and also enable the distal end to be tracked in the field-based frame of reference.

Field-based position sensing systems are typically more accurate than impedance-based position sensing systems. For example, field-based position sensing systems may be accurate to within one millimeter while impedance-based position sensing systems may be accurate to within three millimeters. However, field-based position sensing systems are typically more costly than the impedance-based position sensing systems. Additionally, while field-based position sensing systems are more accurate than impedance-based position sensing systems, field-based position sensing systems are sensitive to metal interference and patient body movements.

Medical systems, typically those using multiple probes during a medical procedure, may incorporate into at least one of the probes an electrode and a field-based position sensor. Such a probe, herein termed a reference probe, may be used to map the volume of the body cavity in both systems, and a correlation between the two mappings may then be applied to other probes having only mapping electrodes, the mapping electrodes being used for tracking the probes in an impedance-based system. In order that the impedance-based location coordinates of the reference probe correspond to its field-based location coordinates, the frames of reference of the two systems are registered, so generating a relation between the two frames of reference. Using the relation typically increases the accuracy of the impedance-based system, as well as allowing the electrode-only probes to be tracked in the field-based system.

The registration may be accomplished by incorporating a field-based sensor into at least one, and typically all, of the patches. The incorporation enables field-based location coordinates of the patches to be measured in the field-based system, and the registration relation may then be computed by comparing the field-based location coordinates of the patches with their impedance-based coordinates.

During the course of a medical procedure, the registration relation may change, for example because of movement of one of the patches. In prior art systems, such a change requires re-registration of the two frames of reference by finding new field-based location coordinates of all the patches. The re-registration is time-consuming and relatively computer-intensive.

Embodiments of the present invention provide methods and systems for managing a change in the relation differently. As described hereinbelow, upon detecting a difference in the registration relation between a first time and a subsequent second time, embodiments of the present invention assume that impedance-based patch coordinates at the subsequent second time are correct, calculate a field-based location coordinate correction, and apply the correction in order to correct the field-based location coordinates of the patches. Unlike the prior art systems referenced supra, applying the correction is less time-consuming, does not require resetting the position sensing system, and does not disturb any medical procedure being performed.

The corrected field-based location coordinates may be used in tracking a magnetic tracking sensor inside the body of the subject, based on signals received by the sensor in response to magnetic fields from the generators that are applied to the subject. The magnetic tracking sensor may be the sensor of the reference probe, or any other magnetic sensor incorporated into another probe used in the medical procedure.

System Description

Figure 1:
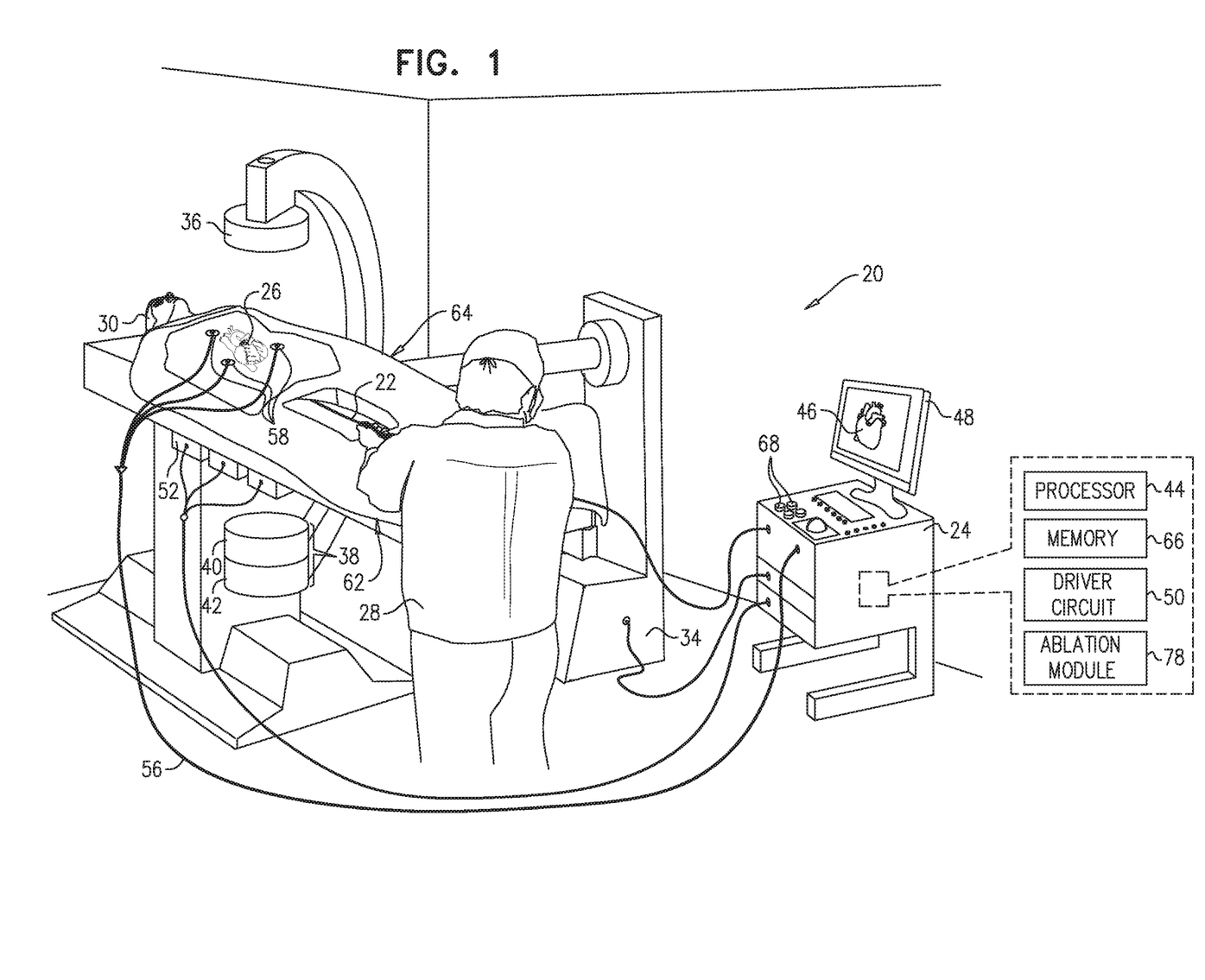
FIG. 1 is a schematic pictorial illustration of a medical system having multiple adhesive skin patches and configured to use impedance-based location coordinates to correct field-based location coordinates of a given skin patch while performing a catheter-based procedure on a heart of a patient, in accordance with an embodiment of the present invention.
Figure 2:
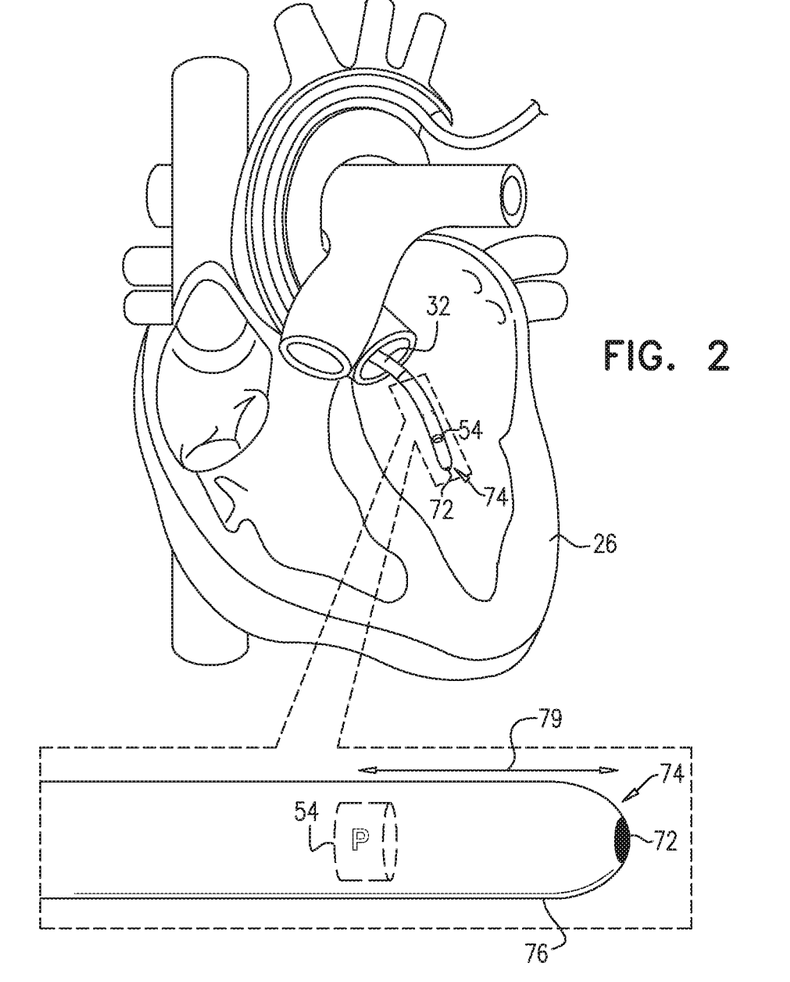
FIG. 2 is a schematic pictorial illustration of the catheter in the heart, in accordance with an embodiment of the present invention.

FIG. 1 is a schematic pictorial illustration of a medical system 20, and FIG. 2 is a schematic illustration of a probe used in the system, in accordance with an embodiment of the present invention. System 20 may be based, for example, on the CARTO® system, produced by Biosense Webster Inc. (Diamond Bar, Calif.). System 20 comprises a medical probe 22, such as a catheter, and a control console 24. In embodiments described hereinbelow, it is assumed that probe 22 is used for diagnostic or therapeutic treatment, such as performing ablation of heart tissue in a heart 26. Alternatively, probe 22 may be used, mutatis mutandis, for other therapeutic and/or diagnostic purposes in the heart or in other body organs.

An operator 28 inserts probe 22 through the vascular system of a patient 30 so that a distal end 32 (FIG. 2) of probe 22 enters a chamber of heart 26. In the configuration shown in FIG. 1, operator 28 uses a fluoroscopy unit 34 to visualize distal end 32 inside heart 26. Fluoroscopy unit 34 comprises an X-ray source 36, positioned above patient 30, which transmits X-rays through the patient. A flat panel detector 38, positioned below patient 30, comprises a scintillator layer 40 which converts the X-rays which pass through patient 30 into light, and a sensor layer 42 which converts the light into electrical signals. Sensor layer 42 typically comprises a two dimensional array of photodiodes, where each photodiode generates an electrical signal in proportion to the light detected by the photodiode.

Control console 24 comprises a processor 44 that converts the electrical signals from fluoroscopy unit 34 into an image 46, which the processor presents as information regarding the procedure on a display 48. Display 48 is assumed, by way of example, to comprise a cathode ray tube (CRT) display or a flat panel display such as a liquid crystal display (LCD), light emitting diode (LED) display or a plasma display. However other display devices can also be employed to implement embodiments of the present invention. In some embodiments, display 48 may comprise a touchscreen configured to accept inputs from operator 28, in addition to presenting image 46.

System 20 can use field-based position sensing to determine position coordinates of distal end 32 inside heart 26. In configurations where system 20 uses field-based based position sensing, console 24 comprises a driver circuit 50 which drives field generators 52 to generate magnetic fields within the body of patient 30. Typically, field generators 52 comprise coils, which are placed below the patient at known positions external to patient 30. These coils generate magnetic fields in a predefined working volume that contains heart 26. A magnetic field sensor 54 (also referred to herein as position sensor 54) within distal end 32 of probe 22 generates electrical signals in response to the magnetic fields from the coils, thereby enabling processor 44 to determine the position of distal end 32 within the cardiac chamber. Magnetic field-based position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference.

During a medical procedure, an array of adhesive skin patches 58 are affixed to a back 62 or a front 64 of patient 30. In other words, each of the skin patch in the array is affixed to a surface of the body of patient 30. At least one of the patches comprises one or more magnetic field sensors (e.g., coils) that can measure the magnetic fields produced by field generators 52, and responsively convey the magnetic field measurements to console 24. Based on the magnetic measurements received from the magnetic field sensors (also referred to herein as patch sensors) in a given patch 58, processor 44 can determine a current field-based position, relative to the field generators, of the given skin patch.

Each patch 58 also comprises a body surface electrode in contact with the surface of the body, and console 24 is connected by a cable 56 to the body surface electrodes. In the configuration shown in FIG. 2, distal end 32 is enveloped by an insulating exterior surface 76, and comprises a probe electrode 72 that typically comprises one or more thin metal layers formed over insulating exterior surface 76 at the distal tip.

In operation, processor 44 can determine impedance-based location coordinates of distal end 32 inside heart 26 based on the impedances measured between the probe electrode and patches 58. Impedance-based position tracking techniques are described, for example, in U.S. Pat. Nos. 5,983,126, 6,456,864 and 5,944,022, whose disclosures are incorporated herein by reference. In embodiments of the present invention, processor 44 can use a distance 79 between position sensor 54 and electrode 72 when performing a registration between the position-dependent magnetic signals received from the magnetic field sensor and position-dependent electrical signals (i.e., impedance measurements) received from patches 58.

In operation, system 20 can use electrode 72 for both impedance-based location sensing and for other activities such as potential acquisition for electrical mapping of the heart, or ablation. Console 24 also comprises a radio frequency (RF) ablation module 78 that delivers electrical power to electrode 72. Processor 44 uses ablation module 78 to monitor and control ablation parameters such as the level of ablation power applied via electrode 72. Ablation module 78 may also monitor and control the duration of the ablation that is provided.

Processor 44 receives and processes the signals generated by position sensor 54 in order to determine field-based position coordinates of distal end 32, typically including both field-based location and field-based orientation coordinates. In addition to determining the field-based coordinates of distal end 32, processor 44 can also receive and process impedances from patches 58 in order to determine electrical-based location coordinates of the distal end. The method of position sensing described hereinabove is implemented in the above-mentioned CARTO® system and is described in detail in the patents and patent application cited above.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

Based on the signals received from probe 22 and other components of system 20, processor 44 drives display 48 to update image 46, so as to present a current position of distal end 32 in the patient's body, as well as to present status information and guidance regarding the procedure that is in progress. Processor 44 stores data representing image 46 in a memory 66. In some embodiments, operator 28 can manipulate image 46 using one or more input devices 68. In embodiments where display 48 comprises a touchscreen display, operator 28 can manipulate image 46 via the touchscreen display.

Field-Based Location Coordinate Correction

Figure 3:
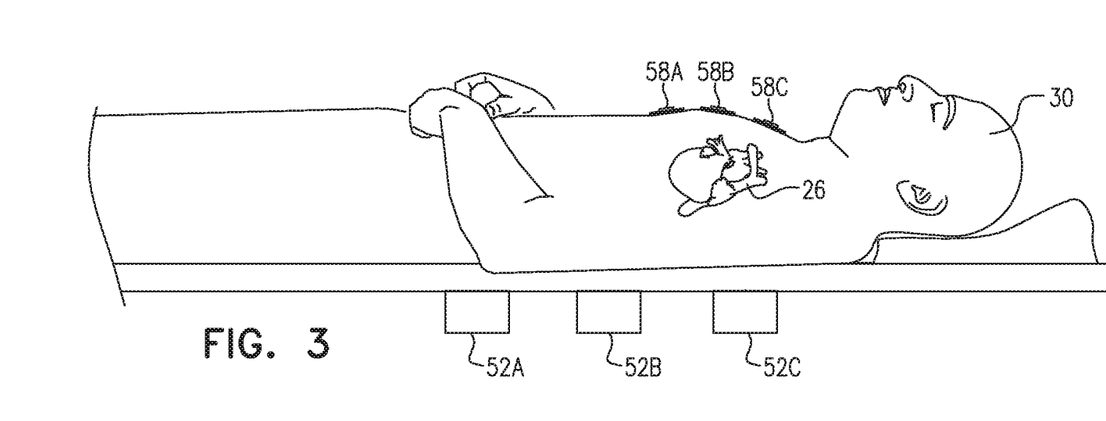
FIG. 3 is a schematic pictorial illustration showing how magnetic fields applied to the patient can be used to determine respective field-based location coordinates for the adhesive skin patches, in accordance with an embodiment of the present invention.

FIG. 3 is a schematic pictorial illustration showing how processor 44 can determine respective field-based location coordinates of adhesive skin patches 58 based on signals conveyed by the adhesive skin patches in response to magnetic fields generated by field generators 52, in accordance with an embodiment of the present invention. In FIG. 3 (and the description referencing FIG. 4 hereinbelow), field generators and adhesive skin patches 58 can be differentiated by appending a letter to the identifying numeral, so that the field generators comprise field generators 52A-52C, and the adhesive skin patches comprise patches 58A-58C.

In operation, the one or more magnetic field sensors in each patch 58 transmits, to control console 24, a signal in response to magnetic fields received at the patches from field generators 52A, 52B and 52C. Upon receiving the signals, processor 44 can process the signals in order to compute respective three-dimensional field-based location coordinates, measured with respect to a field generator frame of reference defined by the fixed positions of the field generators, of patches 58.

Figure 4:
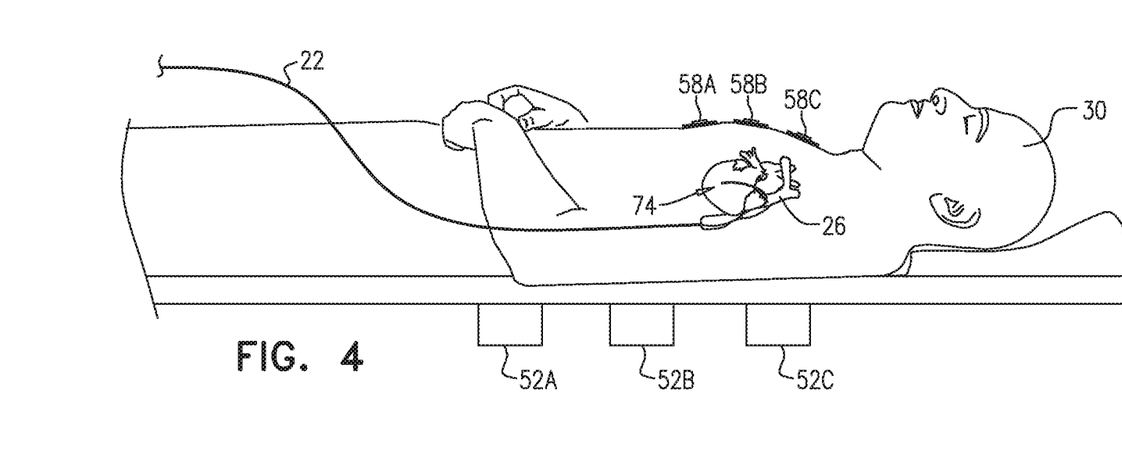
FIG. 4 is a schematic pictorial illustration showing how an electrical current delivered to a body of a patient can be used to determine respective impedance-based location coordinates for the adhesive skin patches, in accordance with an embodiment of the present invention.

FIG. 4 is a schematic pictorial illustration showing how processor 44 can determine respective impedance-based location coordinates of adhesive skin patches 58 based on signals conveyed by the adhesive skin patches in response to an electrical current applied to the body by electrode 72, in accordance with an embodiment of the present invention.

In operation, position sensor 54 transmits, to control console 24, first signals in response to magnetic fields generated by field generators 52A, 52B and 52C. Upon receiving the first signals, processor 44 can process the first signals in order to compute three-dimensional field-based location coordinates of distal tip 74 in the field generator frame of reference.

Additionally, as operator 28 manipulates distal end 32 of the probe within the patient's body, control console 24 conveys an electrical current to electrode 72, and the probe electrode delivers the conveyed electrical current to the patient's body. The electrical current delivered by the probe electrode to the body is divided among patches 58. Therefore, the body surface electrode in each patch 58 receives a respective fraction of the delivered electrical current, each of the fractions depending on an impedance between electrode 72 and a given patch 58. In response to receiving its respective fraction of the delivered electrical current, the body surface electrode in each given patch 58 transmits, to control console 24, a second signal indicating the impedance (i.e., to the electrical current delivered by electrode 72) caused by the body of patient 30.

Upon receiving the second signals, processor 44 can process the signals in order to measure the impedances, and compute a position of electrode 72, based on the measured impedances, in a patch frame of reference defined by the positions of the patches. Since the positions of the patches are known in the field generator frame of reference, processor 44 is able to register the two frames of reference to each other.

Figure 5:
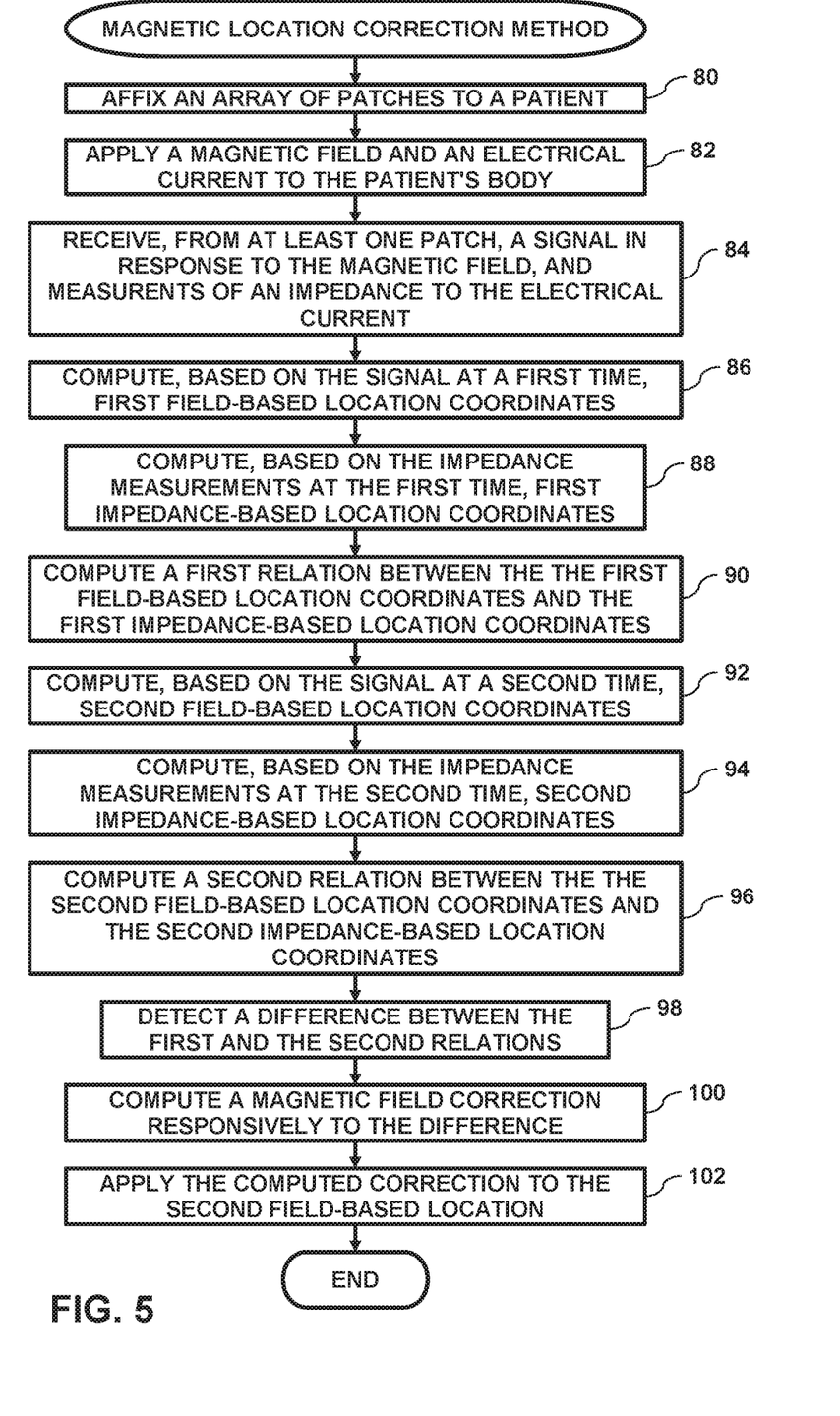
FIG. 5 is a flow diagram that illustrates a method of using impedance-based location coordinates to correct field-based location coordinates of the given skin patch, in accordance with an embodiment of the present invention.
Figure 6A:
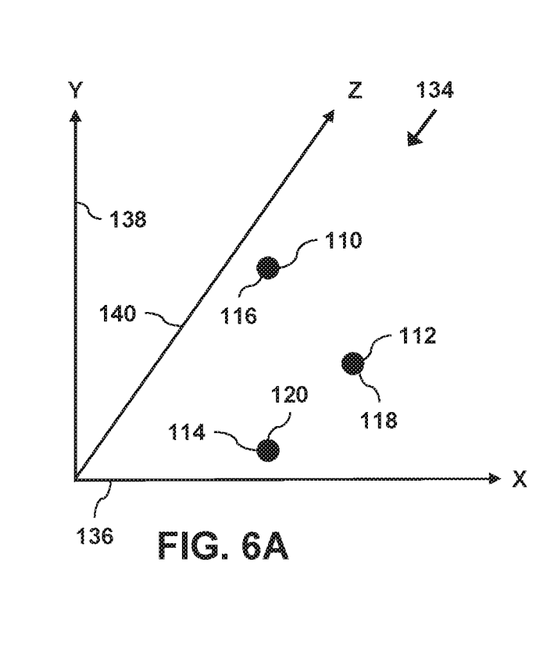
FIGS. 6A-6B are schematic diagrams illustrating, for the adhesive skin patches, first and second field-based location coordinates, first and second impedance-based location coordinates, and corrected second field-based location coordinates, in accordance with an embodiment of the present invention.
Figure 6B:
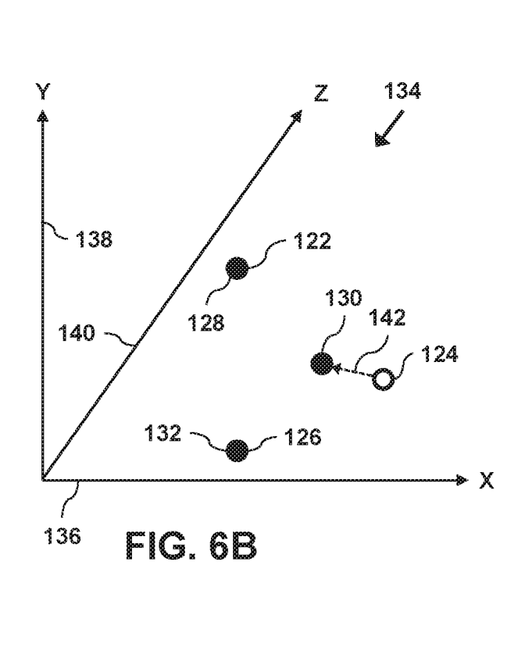

FIG. 5 is a flow diagram that illustrates a method of correcting inconsistent field-based location coordinates of one or more adhesive skin patches 58, and FIGS. 6A and 6B, referred to collectively as FIG. 6, are schematic diagrams illustrating first patch field-based location coordinates 110, 112, 114, first patch impedance-based location coordinates 116, 118, 120, second patch field-based location coordinates 122, 124, 126, and second patch impedance-based location coordinates 128, 130, 132, in accordance with an embodiment of the present invention. In the example shown in FIG. 6, locations 110-132 comprise three-dimensional coordinates in a coordinate system 134 comprising an X-axis 136, a Y-axis 138, and a Z-axis 140.

In an initial step 80, operator 28 affixes primary adhesive skin patches 58 to patient 30. In an application step 82, each field generator 52 applies a respective magnetic field to the body of patient 30, and control console 24 conveys an electrical current to electrode 72, thereby delivering the electrical current to the patient's body. In a receive step 84, processor 44 receives, from at least one patch 58, a signal in response to the magnetic field and measurements of an impedance to the electrical current being applied to the body. Receiving the signal and the impedance measurements is described supra in the description referencing FIGS. 3 and 4.

In a first compute step 86, processor 44 processes the received signal and computes, based on the signal at a first time, first patch field-based coordinates 110, 112 and 114. In a second compute step 88, the processor computes, based on impedance measurements at the first time, first patch impedance-based location coordinates 116, 118 and 120. In the example shown in FIG. 6A, field-based coordinates 110 correspond to, and are approximately the same as, impedance-base coordinates 116, field-based coordinates 112 correspond to, and are approximately the same as, impedance-base coordinates 118, and field-based coordinates 114 correspond to, and are approximately the same as, impedance-base coordinates 120.

In a third compute step 90, processor 44 computes a first relation between first field-based location coordinates 110, 112, 114 and first impedance-based location coordinates 116, 118, 120. In some embodiments, the first relation comprises a distance and an orientation between each of the first location coordinates and the corresponding first impedance-based location coordinates.

It will be understood that computing the first relation corresponds to registering the field generator frame of reference with the patch frame of reference (since the latter is impedance based). Processor 44 uses the first relation to perform a correspondence between impedance-based location coordinates 116 and field-based location coordinates 110, between impedance-based location coordinates 118 and field-based location coordinates 112, and between impedance-based location coordinates 120 and field-based location coordinates 114. Therefore (i.e., due to the correspondence), in the example shown in FIG. 6A, field-based location coordinates 110 are substantially the same as impedance-based location coordinates 116, field-based location coordinates 112 are substantially the same as impedance-based location coordinates 118, and field-based location coordinates 114 are substantially the same as impedance-based location coordinates 120.

In a fourth compute step 92, processor 44 processes the received signal and computes, based on the signal at a second time subsequent to the first time, second field-based coordinates 122, 124 and 126. In a fifth compute step 94, the processor computes, based on impedance measurements at the first time, first impedance-based location coordinates 128, 130 and 132. In the example shown in FIG. 6B, field-based coordinates 122 correspond to impedance-base coordinates 128, field-based coordinates 124 correspond to impedance-base coordinates 130, and field-based coordinates 126 correspond to impedance-base coordinates 132.

In a sixth compute step 96, processor 44 computes a second relation between second field-based location coordinates 122, 124, 126 and second impedance-based location coordinates 128, 130, 132. In some embodiments, the second relation comprises a distance and an orientation between each of the second field-based location coordinates and the corresponding second impedance-based location coordinates.

In a detection step 98, processor 44 detects a discrepancy between the first and the second relations. The detected discrepancy is typically a result of inconsistent second field-based location coordinates relative to corresponding second impedance-based location coordinates for one or more patches 58. In some embodiments, the inconsistent second field-based location coordinates are a result of metal interference (i.e., a metal object in proximity to the patches and/or the field generators) or a movement of the patient's body.

In some embodiments, processor 44 detects the discrepancy between the first and the second relations upon applying the first relation to the second impedance-based location coordinates. In the example shown in FIG. 6B, the discrepancy for a given patch 58 is presented as an arrow 142 comprising a distance and an orientation between impedance-based location coordinates 130 and field-based location coordinates 124.

In response to the detected difference, processor 44 computes a field-based location coordinate correction in a seventh compute step 100. The processor may apply the correction to the inconsistent field-based location coordinates in a correction step 102, so as to re-register the two frames of reference, and the method ends. In some embodiments, the field-based location coordinate correction for a given patch 58 comprises applying the respective distance and orientation in the first relation to the second impedance-based location coordinates.

In the example shown in FIG. 6B, embodiments of the present invention correct impedance-based location coordinates 124 for a given patch 58 by using the first relation (i.e., that was used to register impedance-based location coordinates 118 to field-based location coordinates 112) to register field-based location coordinates 120 to impedance-based location coordinates 130. As indicated by arrow 142, processor 44 uses the first relation to correct field-based location coordinates 124 so that the corrected field-based location coordinates are substantially the same as impedance-based location coordinates 130.

Once processor 44 has calculated the field-based location correction for patches 58, processor 44 can apply the field-based location correction to the signal and the measured impedance indicating subsequent locations of the adhesive skin patches. Therefore, at a third time subsequent to the second time, processor 58 can process the signal so as to compute third field-based location coordinates of the at least one of the patches, compute third impedance-based location coordinates of the at least one of the patches by measuring the impedance to the electrical current, and apply the field-based location coordinate correction to the third field-based location coordinates.

In embodiments of the present invention, processor 44 can track an object (e.g., probe 22) in the patient's body relative to the respective field-based location coordinates of patches 58 while applying the respective location corrections to the respective field-based location coordinates of the patches. Additionally, while embodiments described herein use three adhesive skin patches 58, configurations comprising more than three patches 58 are considered to be within the spirit and scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for sensing, using an array of patches fixed to a surface of a body of a subject, the patches including respective electrodes in contact with the surface, and at least one of the patches including a patch sensor configured to output a signal in response to a magnetic field applied to the body, the method comprising:
    applying the magnetic field to the body generated by one or more field generators external to the body;
    at a first time, processing the signal output in response to the magnetic field applied to the body so as to compute first field-based location coordinates of the at least one of the patches, and computing first impedance-based location coordinates of the at least one of the patches by measuring an impedance between the at least one of the patches and an electrode inside the body;
    at a second time, subsequent to the first time, processing the signal output in response to the magnetic field applied to the body so as to compute second field-based location coordinates of the at least one of the patches, and computing second impedance-based location coordinates of the at least one of the patches by measuring the impedance between the at least one of the patches and the electrode inside the body;
    computing a first relation between the first field-based location coordinates and the first impedance-based location coordinates, and a second relation between the second field-based location coordinates and the second impedance-based location coordinates;
    when there is a difference between the second relation and the first relation, computing a field-based location coordinate correction responsive to the difference between the second relation and the first relation; and
    applying the field-based location coordinate correction in tracking a position of a magnetic tracking sensor inside the body, based on signals received from the magnetic tracking sensor in response to the applied magnetic field.

2. The method according to claim 1, wherein the first relation for the at least one of the patches comprises a first distance and a first orientation between the first impedance-based location coordinates of the at least one of the patches to the first field-based location coordinates of the at least one of the patches, and wherein the second relation for the at least one of the patches comprises a second distance and a second orientation between the second impedance-based location coordinates of the at least one of the patches to the second field-based location coordinates of the at least one of the patches.

3. The method according to claim 2, further comprising the step of computing corrected second field-based location coordinates based on the second impedance-based location coordinates and the first distance and first orientation.

4. The method according to claim 1, and comprising at a third time, subsequent to the second time, processing the signal so as to compute third field-based location coordinates of the at least one of the patches, computing third impedance-based location coordinates of the at least one of the patches by measuring the impedance between the at least one of the patches and the electrode in the body, and applying the field-based location coordinate correction to the third field-based location coordinates.

5. The method according to claim 1, wherein the magnetic field is applied to the body by positioning the body over multiple coils configured to generate the magnetic field.

6. The method according to claim 1, wherein the magnetic tracking sensor is comprised in a medical probe, and the electrode inside the body comprises a probe electrode located at a distal end of the medical probe.

7. The method according to claim 6, wherein the signal comprises a first signal, and wherein measuring the impedance comprises receiving, from the at least one of the patches, a second signal in response to the impedance of electrical current delivered by the probe electrode to the body.

8. The method according to claim 1, wherein the field-based location coordinate correction is based on the second impedance-based location coordinates.

9. An apparatus for sensing, comprising: an array of patches for being fixed to a surface of a body of a subject, the patches including respective electrodes for being placed in contact with the surface, and at least one of the patches including a patch sensor configured to output a signal in response to a magnetic field applied to the body;
    one or more field generators adapted to be located external to the body for generating the magnetic field;
    an electrode for insertion in the body,
    a magnetic tracking sensor for insertion in the body,
    a control console configured:
        at a first time, to process the signal output in response to the magnetic field applied to the body so as to compute first field-based location coordinates of the at least one of the patches, and to compute first impedance-based location coordinates of the at least one of the patches by measuring an impedance between the at least one of the patches and the electrode,
        at a second time, subsequent to the first time, to process the signal output in response to the magnetic field applied to the body so as to compute second field-based location coordinates of the at least one of the patches, and to compute second impedance-based location coordinates of the at least one of the patches by measuring the impedance between the at least one of the patches and the electrode,
        to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction, and to apply the field-based location coordinate correction in tracking a position of the magnetic tracking sensor for insertion in the body, based on signals received from the magnetic tracking sensor in response to the applied magnetic field.

10. The apparatus according to claim 9, wherein the first relation for the at least one of the patches comprises a first distance and a first orientation between the first impedance-based location coordinates of the at least one of the patches to the first field-based location coordinates of the at least one of the patches, and wherein the second relation for the at least one of the patches comprises a second distance and a second orientation between the second impedance-based location coordinates of the at least one of the patches to the second field-based location coordinates of the at least one of the patches.

11. The apparatus according to claim 10, wherein the control console is configured to compute the field-based location coordinate correction by computing corrected field-based location coordinates based on the second impedance-based location coordinates and the first distance and the first orientation.

12. The apparatus according to claim 9, wherein the control console is configured at a third time, subsequent to the second time, to process the signal so as to compute third field-based location coordinates of the at least one of the patches, to compute third impedance-based location coordinates of the at least one of the patches by measuring the impedance between the at least one of the patches and the electrode for insertion in the body, and to apply the field-based location coordinate correction to the third field-based location coordinates.

13. The apparatus according to claim 9, wherein the field generators comprise coils.

14. The apparatus according to claim 9, wherein the magnetic tracking sensor is comprised in a medical probe, and the electrode for insertion in the body comprises a probe electrode located at a distal end of the medical probe.

15. The apparatus according to claim 14, wherein the signal comprises a first signal, and wherein the control console is configured to measure the impedance by receiving, from the at least one of the patches, a second signal in response to the impedance of electrical current delivered by the probe electrode to the body.

16. The apparatus according to claim 9, wherein the field-based location coordinate correction is based on the second impedance-based location coordinates.

* * * * *